United States Patent [19]

Van Wingerden

[11] Patent Number: Plant 6,754

[45] Date of Patent: Apr. 25, 1989

[54] CHRYSANTHEMUM NAMED CALIFORNIA GOLDDUST

[75] Inventor: Rene Van Wingerden, Carpinteria, Calif.

[73] Assignee: California Plant Company, Carpinteria, Calif.

[21] Appl. No.: 138,141

[22] Filed: Dec. 28, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Charles W. Rummler

[57] ABSTRACT

A new variety of *Chrysanthemum morifolium* of the spray type particularly distinguished by its pale yellow blossoms, the petals of which are whorled on the receptacle in a double formation having a very close imbricated arrangement providing a rather solid appearing flower. The plant has a profuse recurrent production of flowers borne singly on stems forming part of the spray formation, the blooming habit being under controlled photoperiod growing conditions. The flowers are borne on individual stems of about eight inches in average length comprising parts of spray formations carried on tall main stems, the plant itself having a prolific branching character, if pinched, with a vigorous, upright growth habit and a total height of three to four feet.

1 Drawing Sheet

BACKGROUND OF THE INVENTION

This new Chrysanthemum variety was discovered by me on Oct. 1, 1987, as a sport of the variety 'Moneymaker' (patent applied for) being grown in my nursery at Carpinteria, Calif. The new flower with its bright light yellow coloration and the relatively dense imbrication of its relatively broad petals was noticed immediately as I inspected the field of 'Moneymaker' being grown to provide stem cuttings for commercial propagation at the nursery of Westland Floral in Carpinteria. Continued propagation of my new discovery provided a fair showing that the novel characteristics of this new variety would hold true from generation to generation and appeared to be firmly fixed. Propagation of this new plant is being carried on at the Westland Floral Nursery by means of stem cuttings.

DESCRIPTION OF THE DRAWINGS

My new Chrysanthemum variety is illustrated by the accompanying drawings, which in the upper view shows a group of flowering stems of the new plant to illustrate the general character and its profuse production of blooms; and in the lower view shows a group of the flowers, one of which has been hand painted to show the true color of the novel blossom.

DESCRIPTION OF THE NEW VARIETY

The following is a detailed description of my new Chrysanthemum variety based upon observation made in the early Fall of 1987 at Carpinteria, Calif., the color designations being according to The R.H.S. Colour Chart published by The Royal Horticultural Society of London, England.

THE PLANT

Origin: Sport.

Parentage: 'Moneymaker' (patent applied for).

Classification:

*Botanic.*—*Chrysanthemum morifolium;* Ramat.

*Commercial.*—Chrysanthemum.

Form: Perennial herbaceous bush.

Height: About 90 to 190 cm.

Cane length: About 105 cm.

Branching character: Prolific, if pinched.

Growth habit: Rapid and upright with good strength.

Foliage:

*Quantity.*—Abundant, typically with 16 leaves.

*Leaf size.*—Medium.

*Leaf shape.*—Pinnately lobed with serrated margin.

*Texture.*—Leathery.

*Color.*—Upper side — 147-A. Under side — 147-B.

*Ribs and veins.*—Prominent.

*Petioles.*—Length: About 1.5 cm.

*Stipules.*—Number: Two. Size: About 0.7 cm.

THE BUD

Size: When mature and beginning to open.

*Diameter.*—About 1.3 cm. to 1.8 cm.

*Length.*—About 1.4 cm. to 1.8 cm.

Shape: Oval.

Rate of opening: Fairly fast.

Color of Florets: When sepals first divide, 9-D. When petals begin to unfurl, 13-B.

Sepals:

*Shape.*—Spear shaped.

*Number.*—About 18.

*Character.*—The sepals are hooded over the bud and are attached together at the base, but are separated at their distal ends and upon opening of the flower, the sepals curl back.

*Color.*—Inside, 138-A. Outside, 137-B.

*Striae.*—The sepals are slightly striated.

Calyx:

*Shape.*—Funnel shaped.

*Size.*—Broad.

*Splitting.*—The calyx does split.

*Appearance.*—Smooth.

Flower Stem:

*Length.*—Up to about 20 cm.

*Character.*—Erect.

*Color.*—144-A.

THE FLOWER

Blooming habit: Recurrent, with controlled photoperiod, and blooming profusely. This plant blooms naturally in the Fall.

Size: Medium.

*Diameter.*—About 6 to 7 cm. when two-thirds open.

*Depth.*—About 1 to 1.5 cm.

Borne: Singly on a stem comprising part of a spray arrangement on a main stem.

Form: When bloom first opens, cup-shaped with higher center. When bloom matures, generally flat.

Petalage:

*Phyllaries.*—About 10 to 12 in number.

*Florets.*—Ray florets: About 28 to 30 in number. Disc florets: About 130 to 150 in number.

*Arrangement.*—Whorled on the receptacle.

*Form.*—Oblong with entire margins and obtuse tip that is slightly serrated.

*Texture.*—Soft.

*Aspect.*—Satiny.

*Color.*—Outer floret: Body — 10-B. Base —9-B/C. Reverse side — 2-D. Inside petal: Body — 12-A. Base — 9-A. Immature distal tips — 7-A. Reverse side — 6-D.

Flower stem:

*Length.*—About 8 to 20 cm.

*Character.*—Upright and rigid.

Effect of weather: The color fades slightly in hot weather.

Discoloration after full bloom: The ray petals become slightly lighter in color.

Persistence: The flowers hang on and dry.

Fragrance: Typical for Chrysanthemum.

Lasting Quality: Good, both on the plant and as a cut flower.

THE REPRODUCTIVE ORGANS

Stamens and anthers: None.

Pistils:

*Number.*—About 150 to 180.

*Styles.*—About 0.6 cm. in length. Color: 5-C.

*Stigmas.*—Color: 5-A.

Character of ovaries: The ovaries are small, slender, and white in color.

This new variety of Chrysanthemum most nearly resembles 'Moneymaker' in its general physiology but differs materially in the color of its ray florets and the appearance of the disc. The difference between the sport and its parent is shown by the following flower comparison table which is based upon direct comparisons made at Westland Floral Nursery at Carpinteria, Calif.

FLOWER COMPARISON TABLE

| | | 'Moneymaker' | 'California GoldDust' |
|---|---|---|---|
| Petalage: | No. of Ray Florets | 30–33 | 28–30 |
| | No. of Disc Florets | 160–180 | 130–150 |
| Ray Floret: | Body Color | 75-D | 10-B |
| | Reverse Color | 56-D | 2-D |
| | Base Color | 154-A | 9-B/C |
| Disc Floret: | Body Color | 75-D | 12-D |
| | Reverse Color | 56-D | 6-D |
| | Base Color | 151-B | 9-A |
| | Distal Tips | 179-D | 7-A |

I claim:

1. A new and distinct variety of Chrysanthemum plant and the parts thereof, substantially as herein shown and described, characterized by its profuse recurrent production of medium sized flowers of a bright yellow coloration borne on straight stems forming part of a general spray formation on a tall flowering stem, the plant branching prolifically, if pinched, with vigorous, upright flowering stems of good strength.

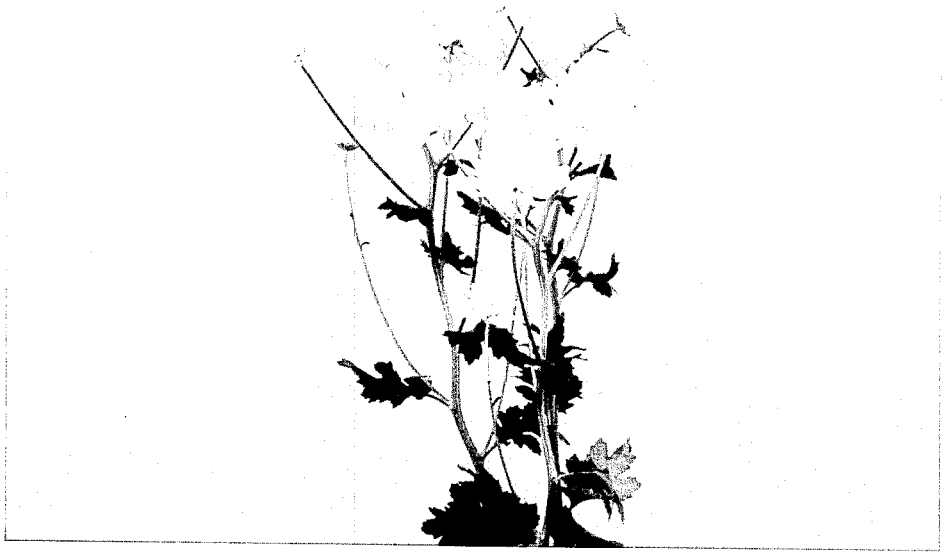

* * * * *